United States Patent
Solovay et al.

(10) Patent No.: US 6,805,706 B2
(45) Date of Patent: Oct. 19, 2004

(54) STENT-GRAFT WITH RAILS

(75) Inventors: Kenneth S. Solovay, Weston, FL (US); Thomas P. Jacobs, Delray Beach, FL (US)

(73) Assignee: GMP Cardiac Care, Inc., Fort Lauderdale, FL (US)

( * ) Notice: Subject to any disclaimer, the term of this patent is extended or adjusted under 35 U.S.C. 154(b) by 0 days.

(21) Appl. No.: 10/641,284

(22) Filed: Aug. 15, 2003

(65) Prior Publication Data

US 2004/0106980 A1 Jun. 3, 2004

Related U.S. Application Data

(60) Provisional application No. 60/403,361, filed on Aug. 15, 2002.

(51) Int. Cl.[7] .................................................. A61F 2/06
(52) U.S. Cl. ..................................... 623/1.15; 623/1.13
(58) Field of Search ............................... 623/1.15, 1.13, 623/1.16, 1.17, 1.18–1.22, 1.35

(56) References Cited

U.S. PATENT DOCUMENTS

| | | | |
|---|---|---|---|
| 3,657,744 A | 4/1972 | Ersek |
| 4,503,569 A | 3/1985 | Dotter |
| 4,512,338 A | 4/1985 | Balko et al. |
| 4,553,545 A | 11/1985 | Maass et al. |
| 4,580,568 A | 4/1986 | Gianturco |
| 4,655,771 A | 4/1987 | Wallsten |
| 4,665,906 A | 5/1987 | Jervis |
| 4,733,665 A | 3/1988 | Palmaz |
| 4,739,762 A | 4/1988 | Palmaz |
| 4,776,337 A | 10/1988 | Palmaz |
| 4,793,348 A | 12/1988 | Palmaz |
| 4,800,882 A | 1/1989 | Gianturco |
| 4,830,003 A | 5/1989 | Wolff et al. |
| 4,856,516 A | 8/1989 | Hillstead |
| 4,886,062 A | 12/1989 | Wiktor |
| 4,907,336 A | 3/1990 | Gianturco |
| 4,950,227 A | 8/1990 | Savin et al. |

(List continued on next page.)

FOREIGN PATENT DOCUMENTS

| | | |
|---|---|---|
| FR | 2714816 | 7/1995 |
| WO | WO 96 41591 | 12/1996 |
| WO | WO 98 20810 | 5/1998 |
| WO | WO 01 15633 | 3/2001 |
| WO | WO 02 074198 | 9/2002 |

OTHER PUBLICATIONS

PCT/US03/25538, International Search Report, dated Dec. 9, 2003.

*Primary Examiner*—Corrine McDermott
*Assistant Examiner*—Hieu Phan
(74) *Attorney, Agent, or Firm*—Banner & Witcoff, Ltd.

(57) ABSTRACT

A stent-graft with increased longitudinal flexibility that is deployed within a body lumen for supporting the lumen and repairing luminal aneurysms. In a preferred embodiment, the stent-graft is located and expanded within a blood vessel to repair aortic aneurysms. The stent-graft is comprised of an expandable stent portion, an expandable graft portion and at least one elongated rail. The stent portion and graft portion are moveable between the terminal ends of the rail(s) and relative to the rails so that it can conform to the shape of a vessel in which it is deployed. The stent-graft provides increased longitudinal flexibility within a vessel. Also, the stent-graft of the present invention does not kink after expansion, and thus, eliminates the potential for the graft portion occluding the blood flow lumen of the vessel in which it is deployed. Moreover, the wear on the graft is reduced and its longevity increased.

52 Claims, 13 Drawing Sheets

U.S. PATENT DOCUMENTS

| | | |
|---|---|---|
| 4,994,071 A | 2/1991 | MacGregor |
| 5,019,085 A | 5/1991 | Hillstead |
| 5,019,090 A | 5/1991 | Pinchuk |
| 5,035,706 A | 7/1991 | Giantureo et al. |
| 5,041,126 A | 8/1991 | Gianturco |
| 5,057,092 A | 10/1991 | Webster, Jr. |
| 5,064,435 A | 11/1991 | Porter |
| 5,067,957 A | 11/1991 | Jervis |
| 5,071,407 A | 12/1991 | Termin et al. |
| 5,102,417 A | 4/1992 | Palmaz |
| 5,104,404 A | 4/1992 | Wolff |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,163,958 A | 11/1992 | Pinchuk |
| 5,190,546 A | 3/1993 | Jervis |
| 5,192,307 A | 3/1993 | Wall |
| 5,197,978 A | 3/1993 | Hess |
| 5,221,261 A | 6/1993 | Termin et al. |
| 5,282,824 A | 2/1994 | Gianturco |
| 5,290,305 A | 3/1994 | Inoue |
| 5,292,331 A | 3/1994 | Boneau |
| 5,354,309 A | 10/1994 | Schnepp-Pesch et al. |
| 5,378,239 A | 1/1995 | Termin et al. |
| 5,395,390 A | 3/1995 | Simon et al. |
| 5,397,345 A | 3/1995 | Lazarus |
| 5,403,341 A | 4/1995 | Solar |
| 5,405,377 A | 4/1995 | Cragg |
| 5,421,955 A | 6/1995 | Lau et al. |
| 5,433,723 A | 7/1995 | Lindenberg et al. |
| 5,443,496 A | 8/1995 | Schwartz et al. |
| 5,449,373 A | 9/1995 | Pinchasik et al. |
| 5,487,858 A | 1/1996 | Schmitt |
| 5,507,767 A | 4/1996 | Maeda et al. |
| 5,507,771 A | 4/1996 | Gianturco |
| 5,540,712 A | 7/1996 | Kleshinski et al. |
| 5,540,713 A | 7/1996 | Schnepp-Pesch et al. |
| 5,545,210 A | 8/1996 | Hess et al. |
| 5,549,635 A | 8/1996 | Solar |
| 5,549,662 A | 8/1996 | Fordenbacher |
| 5,549,663 A | 8/1996 | Cottone, Jr. |
| 5,554,181 A | 9/1996 | Das |
| 5,569,295 A | 10/1996 | Lam |
| 5,571,173 A | 11/1996 | Parodi |
| 5,575,816 A | 11/1996 | Rudnick et al. |
| 5,591,197 A | 1/1997 | Orth et al. |
| 5,597,378 A | 1/1997 | Jervis |
| 5,601,593 A | 2/1997 | Freitag |
| 5,607,445 A | 3/1997 | Summers |
| 5,632,771 A | 5/1997 | Boatman et al. |
| 5,643,312 A | 7/1997 | Fischell et al. |
| 5,649,952 A | 7/1997 | Lam |
| 5,653,727 A | 8/1997 | Wiktor |
| 5,665,115 A | 9/1997 | Cragg |
| 5,674,241 A | 10/1997 | Bley et al. |
| 5,674,278 A | 10/1997 | Boneau |
| 5,683,448 A | 11/1997 | Cragg |
| 5,693,085 A | 12/1997 | Buirge et al. |
| 5,700,285 A | 12/1997 | Myers et al. |
| 5,702,419 A | 12/1997 | Berry et al. |
| 5,723,003 A | 3/1998 | Winston et al. |
| 5,725,572 A | 3/1998 | Lam et al. |
| 5,733,328 A | 3/1998 | Fordenbacher |
| 5,733,330 A | 3/1998 | Cox |
| 5,735,892 A | 4/1998 | Myers et al. |
| 5,735,893 A | 4/1998 | Lau et al. |
| 5,741,333 A | 4/1998 | Frid |
| 5,746,766 A | 5/1998 | Edoga |
| 5,755,781 A | 5/1998 | Jayaraman |
| 5,766,237 A | 6/1998 | Cragg |
| 5,766,239 A | 6/1998 | Cox |
| 5,769,887 A | 6/1998 | Brown et al. |
| 5,776,181 A | 7/1998 | Lee et al. |
| 5,800,456 A | 9/1998 | Maeda et al. |
| 5,800,515 A | 9/1998 | Nadal et al. |
| 5,817,152 A | 10/1998 | Birdsall et al. |
| 5,843,158 A | 12/1998 | Lenker et al. |
| 5,843,163 A | 12/1998 | Wall |
| 5,843,168 A | 12/1998 | Dang |
| 5,851,228 A | 12/1998 | Pinheiro |
| 5,853,419 A | 12/1998 | Imran |
| 5,868,782 A | 2/1999 | Frantzen |
| 5,868,783 A | 2/1999 | Tower |
| 5,876,432 A | 3/1999 | Lau et al. |
| 5,879,370 A | 3/1999 | Fischell et al. |
| 5,879,381 A | 3/1999 | Moriuchi et al. |
| 5,879,382 A | 3/1999 | Boneau |
| 5,891,190 A | 4/1999 | Boneau |
| 5,902,332 A | 5/1999 | Schatz |
| 5,911,732 A | 6/1999 | Hojeibane |
| 5,919,225 A | 7/1999 | Lau et al. |
| 5,925,061 A | 7/1999 | Ogi et al. |
| 5,938,695 A | 8/1999 | Borghi |
| 5,976,182 A | 11/1999 | Cox |
| 5,984,957 A | 11/1999 | Laptewicz, Jr. et al. |
| 6,010,530 A | 1/2000 | Goicoechea |
| 6,013,854 A | 1/2000 | Moriuchi |
| 6,015,429 A | 1/2000 | Lau et al. |
| 6,015,432 A | 1/2000 | Rakos et al. |
| 6,017,362 A | 1/2000 | Lau |
| 6,022,359 A | 2/2000 | Frantzen |
| 6,033,434 A | 3/2000 | Borghi |
| 6,039,755 A | 3/2000 | Edwin et al. |
| 6,042,605 A | 3/2000 | Martin et al. |
| 6,042,606 A | 3/2000 | Frantzen |
| 6,053,940 A | 4/2000 | Wijay |
| 6,056,775 A | 5/2000 | Borghi et al. |
| 6,066,168 A | 5/2000 | Lau et al. |
| 6,071,307 A | 6/2000 | Rhee et al. |
| 6,077,296 A | 6/2000 | Shokoohi et al. |
| 6,083,259 A | 7/2000 | Frantzen |
| 6,086,604 A | 7/2000 | Fischell et al. |
| 6,099,558 A | 8/2000 | White et al. |
| 6,099,561 A | 8/2000 | Alt |
| 6,113,621 A | 9/2000 | Wiktor |
| 6,113,628 A | 9/2000 | Borghi |
| 6,123,722 A | 9/2000 | Fogarty et al. |
| 6,136,023 A | 10/2000 | Boyle |
| 6,143,022 A | 11/2000 | Shull et al. |
| 6,165,210 A | 12/2000 | Lau et al. |
| 6,171,334 B1 | 1/2001 | Cox |
| 6,174,328 B1 | 1/2001 | Cragg |
| 6,183,507 B1 * | 2/2001 | Lashinski et al. .......... 623/1.15 |
| 6,187,036 B1 * | 2/2001 | Shaolian et al. .......... 623/1.15 |
| 6,190,406 B1 * | 2/2001 | Duerig et al. ............... 623/1.2 |
| 6,200,337 B1 | 3/2001 | Moriuchi et al. |
| 6,217,608 B1 | 4/2001 | Penn et al. |
| 6,221,096 B1 | 4/2001 | Aiba et al. |
| 6,224,625 B1 | 5/2001 | Jayaraman |
| 6,238,409 B1 | 5/2001 | Hojeibane |
| 6,245,100 B1 | 6/2001 | Davila et al. |
| 6,254,630 B1 | 7/2001 | Inoue |
| 6,258,117 B1 | 7/2001 | Camrud et al. |
| 6,264,687 B1 | 7/2001 | Tomonto |
| 6,270,520 B1 | 8/2001 | Inoue |
| 6,270,524 B1 | 8/2001 | Kim |
| 6,273,917 B1 | 8/2001 | Inoue |
| 6,280,467 B1 | 8/2001 | Leonhardt |
| 6,293,966 B1 | 9/2001 | Frantzen |
| 6,296,661 B1 | 10/2001 | Davila et al. |

| | | | | | | |
|---|---|---|---|---|---|---|
| 6,299,635 | B1 | 10/2001 | Frantzen | 6,494,909 B2 | 12/2002 | Greenhalgh |
| 6,306,141 | B1 | 10/2001 | Jervis | 6,514,282 B1 | 2/2003 | Inoue |
| 6,315,791 | B1 | 11/2001 | Gingras et al. | 6,517,570 B1 | 2/2003 | Lau et al. |
| 6,319,278 | B1 | 11/2001 | Quinn | 6,520,986 B2 | 2/2003 | Martin et al. |
| 6,322,585 | B1 | 11/2001 | Khosravi et al. | 6,530,951 B1 | 3/2003 | Bates et al. |
| 6,325,820 | B1 | 12/2001 | Khosravi et al. | 6,533,805 B1 | 3/2003 | Jervis |
| 6,331,188 | B1 | 12/2001 | Lau et al. | 6,533,807 B2 | 3/2003 | Wolinsky et al. |
| 6,334,866 | B1 | 1/2002 | Wall | 6,537,284 B1 | 3/2003 | Inoue |
| 6,334,869 | B1 | 1/2002 | Leonhardt et al. | 6,540,774 B1 | 4/2003 | Cox |
| 6,344,053 | B1 | 2/2002 | Boneau | 6,540,775 B1 | 4/2003 | Fischell et al. |
| 6,355,056 | B1 | 3/2002 | Pinheiro | 6,547,817 B1 | 4/2003 | Fischell et al. |
| 6,358,274 | B1 | 3/2002 | Thompson | 6,551,352 B2 | 4/2003 | Clerc et al. |
| 6,361,637 | B2 | 3/2002 | Martin et al. | 6,554,848 B2 | 4/2003 | Boylan et al. |
| 6,368,345 | B1 | 4/2002 | Dehdashtian et al. | 6,558,396 B1 | 5/2003 | Inoue |
| 6,375,677 | B1 | 4/2002 | Penn et al. | 6,558,414 B2 | 5/2003 | Layne |
| 6,387,122 | B1 | 5/2002 | Cragg | 6,565,596 B1 | 5/2003 | White et al. |
| 6,391,033 | B2 | 5/2002 | Ryan | 6,565,600 B2 | 5/2003 | Hojeibane |
| 6,398,803 | B1 | 6/2002 | Layne et al. | 6,569,191 B1 | 5/2003 | Hogan |
| 6,402,779 | B1 | 6/2002 | Colone et al. | 6,569,195 B2 | 5/2003 | Yang et al. |
| 6,409,752 | B1 | 6/2002 | Boatman et al. | 6,572,646 B1 | 6/2003 | Boylan et al. |
| 6,416,539 | B1 | 7/2002 | Hassdenteufel | 6,579,307 B2 | 6/2003 | Sarac |
| 6,451,025 | B1 | 9/2002 | Jervis | 6,579,310 B1 | 6/2003 | Cox et al. |
| 6,451,050 | B1 | 9/2002 | Rudakov et al. | 6,585,757 B1 | 7/2003 | Callol |
| 6,451,051 | B2 | 9/2002 | Drasler et al. | 2002/0045933 A1 | 4/2002 | Jang |
| 6,464,719 | B2 | 10/2002 | Jayaraman | 2002/0143386 A1 | 10/2002 | Davila et al. |
| 6,464,722 | B2 | 10/2002 | Israel et al. | | | |
| 6,471,722 | B1 | 10/2002 | Inoue | | | |
| 6,485,511 | B2 | 11/2002 | Lau et al. | | | |

\* cited by examiner

STENT-GRAFT WITH RAILS

RELATED APPLICATION

This application claims the benefit of and incorporates by reference U.S. Provisional Patent Application No. 60/403,361 filed on Aug. 15, 2002.

FIELD OF THE INVENTION

The present invention relates to a stent-graft for use as a prosthetic within a body lumen to support the lumen, and particularly, to a stent-graft having improved longitudinal structural flexibility and graft wear that can be used within a body to support a lumen.

BACKGROUND OF THE INVENTION

It is generally known to insert a resiliently expandable stent into a body lumen, such as a blood vessel, to provide radial hoop support within the lumen in the treatment of atherosclerotic stenosis and other conditions. For example, it is generally known to open a blocked cardiac blood vessel by conventional methods (e.g., balloon angioplasty or laser ablation) and to keep that blood vessel open using an expandable stent.

Stents are tubular structures formed of biocompatible materials, usually metals like stainless steel or Nitinol, which are radially expandable. The radial strength of the stent material keeps the stent and the lumen into which the stent is deployed in an open configuration. Expandable stents typically include a mesh-like surface pattern of slots or holes cut therein so that a balloon can expand the stent after the stent has been deployed into the body lumen and positioned at a predetermined location. However, these mesh-like surface patterns also permit the passage of endothelial and other cells through the openings in the stents that can cause restenosis of the vessels. For example, the mesh-like surface patterns can permit thrombus formations and plaque buildup within the vessel.

Expandable stents have been combined with coverings of biocompatible materials to form "stent-grafts" that provide benefits in addition to those provided by conventional expandable stents. For example, the expandable stent-grafts can be used as a graft within a body lumen, such as a blood vessel. Intraluminal vascular stent-grafts can be used to repair aneurysmal vessels, particularly aortic arteries, by inserting an intraluminal vascular stent-graft within the aneurysmal vessel so that the prosthetic stent-graft support the vessel and withstand the forces within the vessel that are responsible for creating the aneurysm.

Polytetrafluroethylene (PTFE) has been used as a material from which to fabricate blood vessel grafts or prostheses used to replace damaged or diseased vessels.

This is partially because PTFE is extremely biocompatible causing little or no immunogenic reaction when placed within the human body. Additionally, in a preferred form, expanded PTFE (ePTFE) has been used. This material is light and porous and is potentially colonized by living cells becoming a permanent part of the body. The process of making ePTFE of vascular graft grade is well known.

Enclosing a stent with ePTFE can create a vascular prosthetic that limits the amount of cellular material that can enter the stent and the blood vessel. However, such a stent-graft tends to be rather inflexible. Conventional stent-grafts tend not to conform to the natural curved shape of the blood vessel in which they are deployed. In particular, conventional stent-grafts can be longitudinally inflexible (i.e., along a length of the stent portion and the graft portion), and therefore tend to be resistant to transverse deformation. As a result, these stent-grafts may not effectively seal the intended aneurysm(s) within the blood vessel in which the stent-graft is deployed.

Conventional stent-grafts include circumferential support members (hoops) that are securely spaced from each other and from the ends of the stent portion so that they do not experience relative axial movement. The spacing between adjacent support elements is maintained by rigid connections or bridge elements (sometimes referred to in the art as "bridges") between adjacent support elements and at least one elongated member that extends from a first end of the stent portion to a second end of the stent portion. The circumferential support members are also secured to the graft portion of material extending along the stent portion so that the graft portion cannot move along the length of the stent portion. These secure, rigid connections prevent the support elements and the graft portion from moving longitudinally along the elongated member(s) of the stent and prevent the stent-graft from conforming to the curvature of the blood vessel in which it is deployed. The interaction of the conventional stent material and the conventional graft material, along with the large expanded diameter of a stent-graft, create conformability, performance and manufacturing issues that are in addition to those issues associated with conventional stents and discussed in copending U.S. patent application Ser. No. 10/100,986 which is hereby incorporated by reference. For example, poor longitudinal flexibility of the stent-graft can lead to kinking of the graft portion and the ultimate occlusion of the flow lumen. Additional disadvantageous of conventional stent-grafts can include graft wear on the stent portion, blood leakage through suture holes in the graft portion that receive the sutures that anchor the graft portion to the stent portion and labor intensive manufacturing processes.

There is a need in the art for a stent-graft that is longitudinally flexible, while providing a smooth inner surface for blood flow.

SUMMARY OF THE INVENTION

The present invention relates to a stent-graft with increased longitudinal flexibility relative to conventional stent-grafts. Longitudinal flexibility as used herein relates to the flexibility of the stent-graft structure (or portions thereof) to move relative to its major, longitudinal axis of extension. The stent-graft is deployed within a body lumen for supporting the lumen and repairing luminal aneurysms. In a preferred embodiment, the stent-graft is located and expanded within a blood vessel to repair aortic aneurysms.

In an embodiment, the stent-graft can be comprised of an expandable stent portion, an expandable graft portion and at least one elongated rail. The stent portion and graft portion are moveable between the terminal ends of the rail(s) and relative to the rails so that the stent-graft can conform to the shape of a vessel in which it is deployed. Additionally, longitudinally adjacent circumferential support elements of the stent portion can be secured together by at least one bridging element. Alternatively, each circumferential support elements can be free of a connection to a longitudinally adjacent circumferential support element. The use of the rail(s) and the bridging elements allows the support elements to separate as needed, assume the outer radius of a vessel bend and shorten to assume an inner radius of a vessel bend. The stent-graft eliminates the poor longitudinal flexibility associated with conventional stent-grafts. As a result, the stent-graft of the present invention provides greater resistance to kinking after expansion, and thus, eliminates the potential for the graft portion occluding the blood flow lumen. Moreover, the wear on the graft is reduced and its longevity increased.

Furthermore, according to an aspect of the present invention, the graft portion of the stent-graft is coupled to at least one longitudinal extending rail at locations spaced from the ends of the stent-graft. In one embodiment, the graft portion is coupled to the rails at the locations spaced from the ends of the stent-graft without the use of sutures that would extend through the graft portion and compromise the fluid retention integrity of the graft portion at these spaced locations. Instead, circumferential coupling members positioned about the graft portion and secured to the graft portion can receive the rails. These coupling members include circumferentially spaced openings that receive the rail(s). Alternatively, the rails extend through cauterized holes that were mechanically created in a substrate of the graft portion. Passing the rail(s) through these openings and holes reduces manufacturing costs and time. Passing the rail(s) also provides greater expanded longitudinal flexibility, prevents apices of the stent portion from protruding into the graft portion and the blood vessel and reduces wear on the material forming the graft portion. The securing of the rail(s) relative to the graft portion according to the present invention eliminates the blood leakage that is typically seen with conventional stent-grafts that employ sutures. In this or any of the embodiments discussed herein, the ends of the graft portion may be secured to the stent portion by sutures.

BRIEF DESCRIPTION OF THE DRAWINGS

The present invention will be even better understood with reference to the attached drawings, in which.

DETAILED DESCRIPTION OF THE INVENTION

Figure 1:
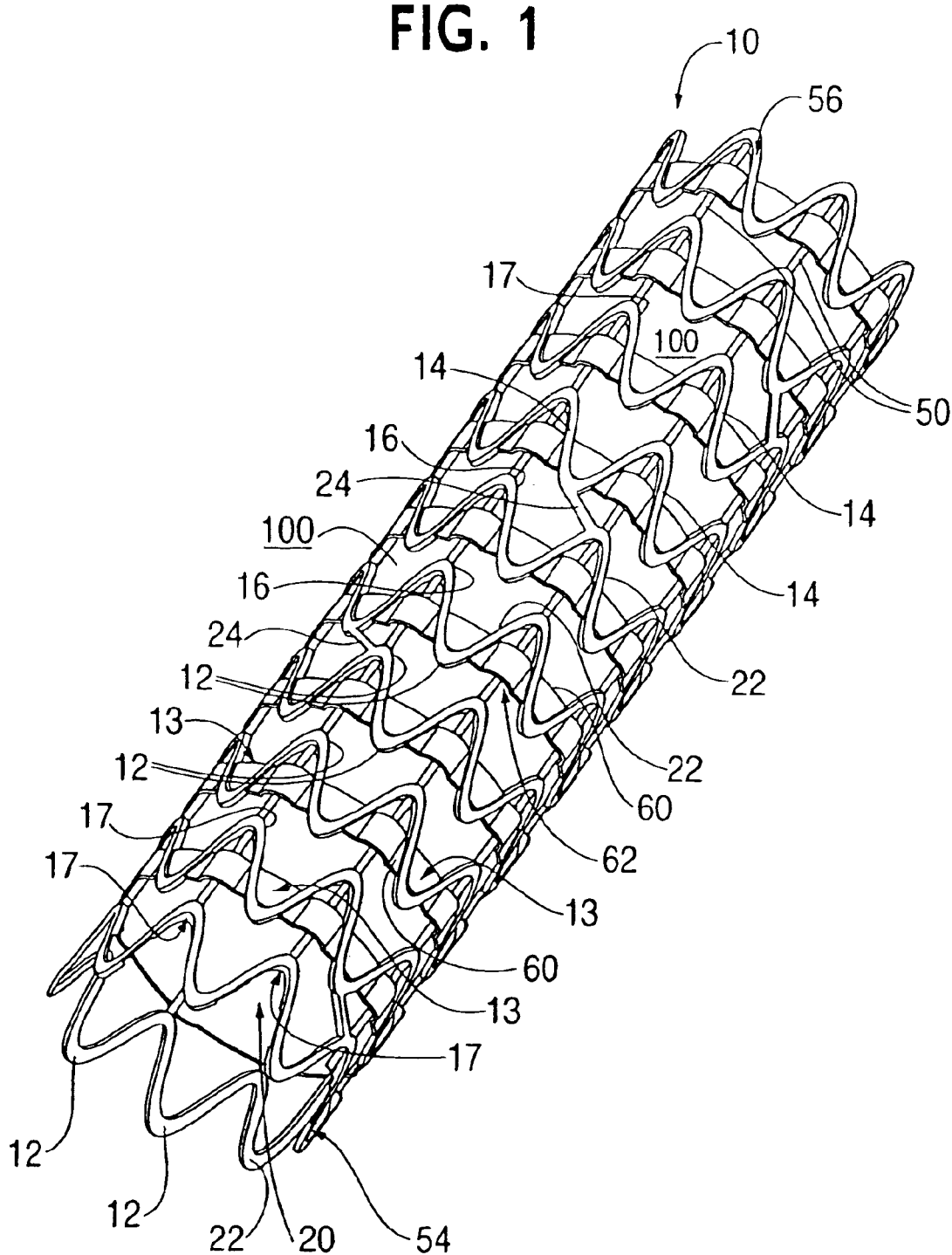
FIG. 1 illustrates a stent-graft according to an embodiment of the present invention.

Referring to the figures where like numerals indicate the same element throughout the views, FIG. 1 illustrates a stent-graft 10 according to the present invention. The stent-graft 10 includes a graft portion 100 and a stent portion 20 with flexible elongated rail elements 50. The stent portion 20 provides support to the graft portion 100 when the stent-graft 10 is deployed and located in an expanded condition within a portion of a mammalian body such as a vascular lumen.

The stent portion 20 includes a plurality of spaced, circumferentially extending support elements (hoops) 22. Each circumferential support element 22 is generally annular in shape as shown in FIG. 1. Each circumferential support element 22 is made from a flexible, biocompatible material (i.e., from a material that is, for example, non-reactive and/or non-irritating). In one embodiment, the stent portion 20 can be formed from a tube of biocompatible material. For example, the stent portion 20 can be formed by laser cutting the stent portion 20 and its support elements 22, etc. from the tube. In another embodiment, each circumferential support element 22 is made from medical-grade metal wire formed as a closed loop (i.e., as an annular hoop) in a known manner, including, for example, micro-welding two ends of a wire segment together.

Stainless steel, metal alloys, shape-memory alloys, super elastic alloys and polymeric materials used in conventional stents are representative examples of materials from which circumferential stent portion 20 and its support elements 22 can be formed. The alloys can include Ni/Ti (Nitinol). The polymers for circumferential support elements 22 may, for example, be bioabsorbable polymers so that the stent can be absorbed into the body instead of being removed.

Figure 2:
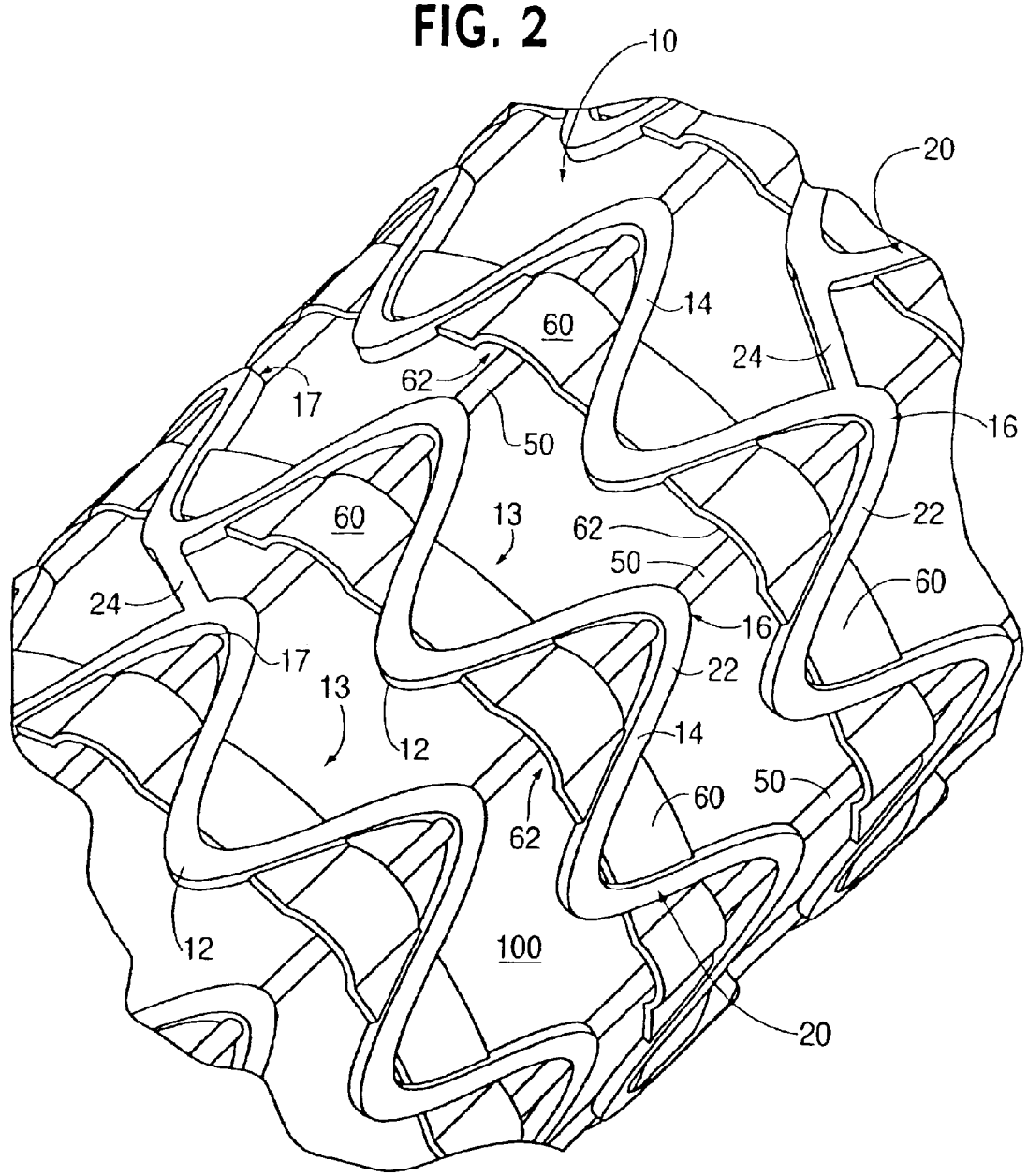
FIG. 2 is an enlarged view of a portion of the stent-graft shown in FIG. 1.
Figure 3:
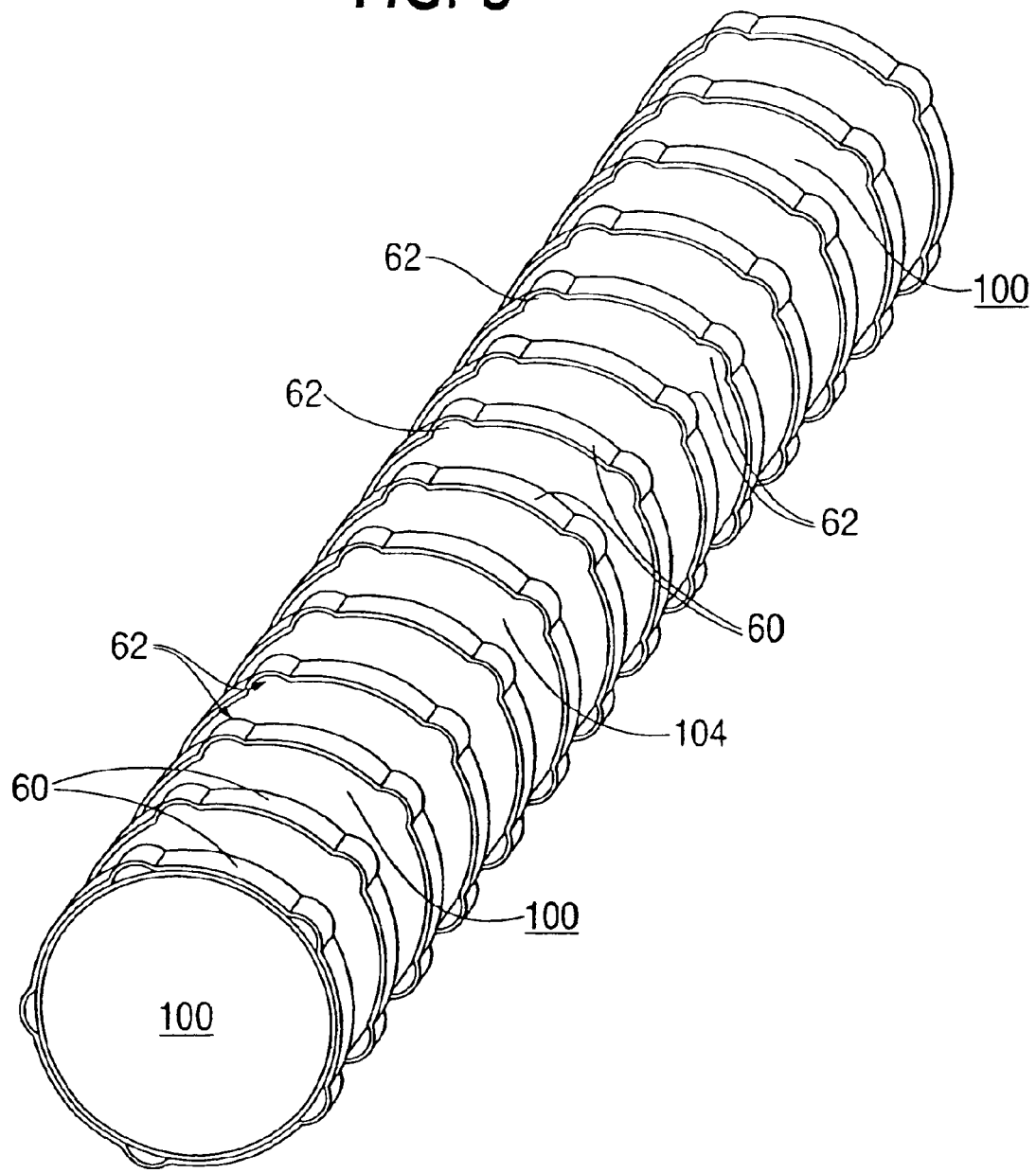
FIG. 3 illustrates a graft portion and rail receiving coupling members of the stent-graft shown in FIG. 1.
Figure 4:
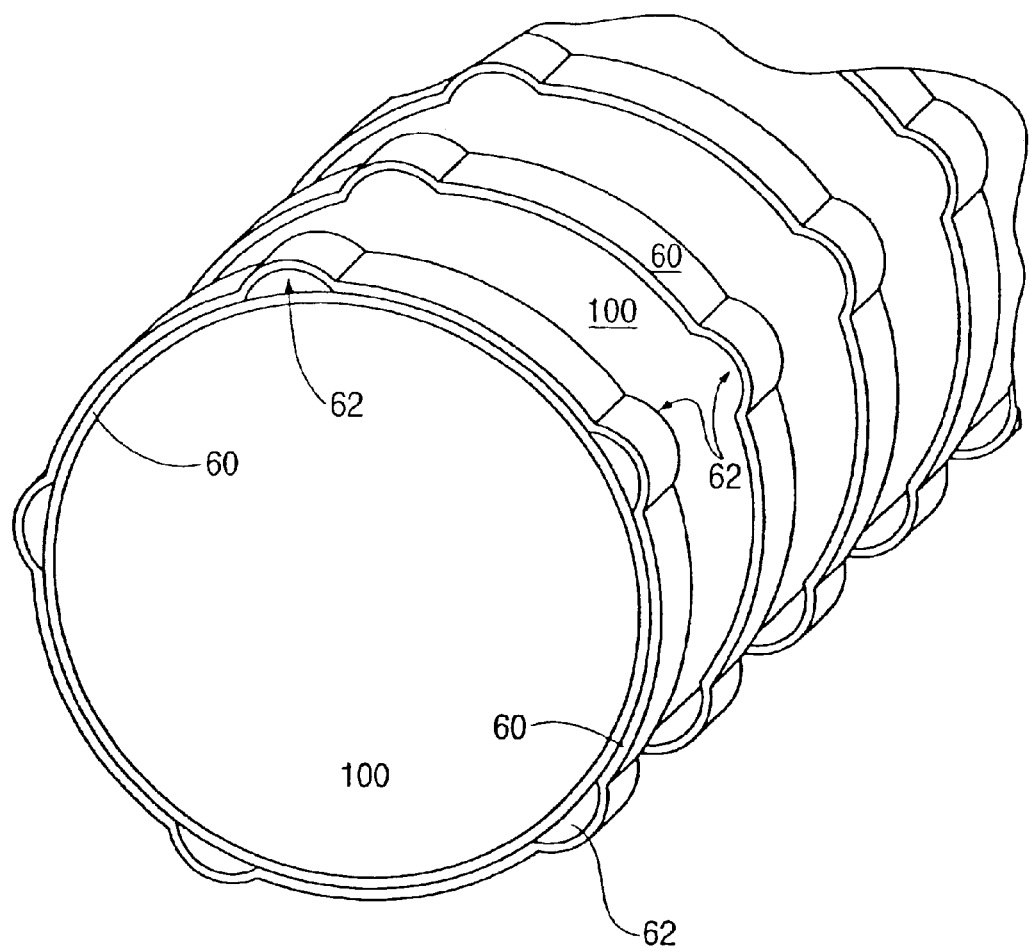
FIG. 4 is an enlarged view of an end of the graft portion and rail receiving coupling members illustrated in FIG. 3.
Figure 8:
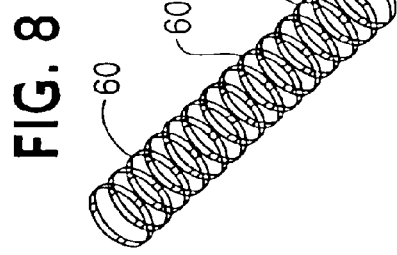
FIG. 8 is a perspective view of the rail receiving coupling members spaced along the stent-graft with the graft portion and stent portion removed.

In a first embodiment, illustrated in FIGS. 1 and 2, each circumferential support element 22 has a sinusoidal or otherwise undulating form, such as a wave shape. As shown in FIGS. 1 and 2, the undulating form of the support elements 22 includes peaks 12 and troughs 13 (space behind the peaks). The troughs 13 include the open spaces between adjacent substantially linear struts 14 that are connected to a curved member 16 that forms the respective peak 12. Each peak 12 points in a direction that is opposite that of the immediately preceding or following, circumferentially positioned peak 12. The same is true of the troughs 13. Each trough 13 points in a direction that is opposite the immediately preceding or following, circumferentially positioned trough.

In the embodiment illustrated in FIGS. 1 and 2, the peaks 12 all face in the one direction, toward a first end 54 of the stent 20. Similarly, the troughs 13 all face in one direction, toward a second end 56 of the stent 20, which is opposite the first end. Each circumferential support element 22 is connected to a longitudinally adjacent circumferential support element 22 by a respective bridge element 24 (FIGS. 1 and 2). As shown, the bridge elements 24 connect peaks of adjacent and circumferentially out-of-phase peaks 12 of adjacent support elements 22. As a result, adjacent support elements 22 can be rigidly spaced from each other at the area where they are joined by the bridge element 24.

In the embodiment shown in FIGS. 1 and 2, only a limited number of bridge elements 24 are provided between respective adjacent support elements 22. For example, adjacent support elements 22 may be connected to each other by between about one and three bridge elements 24. In an embodiment, only one bridge element 24 extends between adjacent support elements 22. If too many bridge elements 24 are provided between adjacent support elements, the coupling between the support elements 22 becomes similar to providing a rigid coupling between support elements, such that the desired longitudinal flexibility according to the present invention is lost. By providing only a limited number of bridge elements 24 (including, without limitation, one bridge element 24), the resultant assembly can still provide a good approximation of using completely independent circumferential support elements 22.

Furthermore, the peripheral location at which bridge element(s) 24 are provided between respective adjacent support elements 22 has an effect on longitudinal flexibility. For example, if two bridge elements are provided between a respective pair of adjacent support elements 22 at diametrically opposite sides of the support elements 22, then, generally, the longitudinal flexibility there between is at a maximum at diametrically opposite sides of the support elements 22 located at about 90 degrees from the bridge elements 24, and decreases along the circumference of the support elements 22 in a direction approaching the respective bridge elements 24.

For the foregoing reasons, it may be useful or otherwise beneficial to provide, for example, one bridge element 24 between adjacent support elements 22, as illustrated in FIG. 1. Furthermore, it may be additionally useful to offset each bridge element 24 from a longitudinally adjacent bridge element 24 in a circumferential direction, as is also illustrated in FIG. 1. The circumferential offset can be staggered by one set of peaks 12 along the length of the stent portion 20 between adjacent support elements 22. Alternatively, the bridge elements 24 can be circumferentially offset by up to 180 degrees for adjacent pairs of support elements 22. The above-discussed circumferential offset embodiments provide the structural integrity benefits of using a bridge element 24, but distribute the resultant restriction in longitudinal flexibility so that no one transverse direction of stent deflection is overly restricted.

In an alternative embodiment illustrated in FIGS. 9–15, the circumferential support elements 22 are formed by a plurality of connected, substantially diamond shaped support members 30. Each diamond shaped support member 30 has a first circumferential peak 32 and a second circumferential peak 33 that point in opposite circumferential directions. Each support member 30 also includes a first longitudinal peak 34 and a second longitudinal peak 35 that point toward different ends of the stent portion 20. Circumferentially successive diamond shaped support members 30 are connected to each other at a junction 36 that is formed as part of the support element 22 during the pressing or molding of the support elements 22. Alternatively, the junctions 36 can be applied using conventional techniques such as welding, hooks or friction fitting.

As shown in FIGS. 1 and 2, the support elements 22 are freely mounted on flexible, elongated rail elements 50 (hereinafter "rails") such that the support elements 22 can move along the rails 50. The rails 50 extend along the length of the stent-graft 10 between the outermost peaks 12 of terminal support elements 22 at a first end 54 and the innermost peaks 12 of the terminal support element 22 at a second end 56. As illustrated, the terminal support elements 22 can extend beyond the terminal ends of the graft-portion 100.

Rails 50 are desirably sufficiently flexible to accommodate bends, curves, etc. in a blood vessel. In one embodiment, the rails 50 are free of longitudinal expansion. Also, the rails 50 may be made from, for example and without limitation the following biocompatible materials: metals, metallic alloys including those discussed above, glass or acrylic, and polymers including bioabsorbable polymers. The rails 50 can have any form. For example, the rails 50 can be solid cylindrical members, such as wires or extrusions with a circular, elliptical or other known cross sections. Alternatively, the rails 50 can be ribbons or spring wires.

In contrast to bridge elements 24 which are generally the same thickness and the circumferential support element 22 that they join and thus relatively inflexible, the thickness of the rails 50 can be designed to provide a desired degree of flexibility to a given stent-graft 10. Each rail 50 can have a thickness (diameter) of about 0.001 inch to about 0.010 inch. In an embodiment, each rail 50 has a thickness of about 0.0011 inch to about 0.005 inch. In another embodiment, each rail 50 has a thickness of about 0.005 inch. The rails 50 can be passed or "snaked" through the circumferential support elements 22 as discussed in copending U.S. patent application Ser. No. 10/100,986, which has been incorporated by reference. Additionally, the rails 50 can be passed through the stent portion 20 and the graft portion 100 as discussed below.

At least some of rails 50 may include end structures for preventing the circumferential support elements 22 from unintentionally passing beyond the ends 54, 56 of the rails 50. The end structures may have several forms as illustrated in copending U.S. patent application Ser. No. 10/100,986, which has been incorporated by reference. In an example, the end structures may be mechanical protrusions or grasp structures by which the endmost circumferential support elements 22 are fixed in place relative to the ends 54, 56 of rails 50. In yet another embodiment, the structures may also be a weld (made by, for example, a laser) for bonding a portion of an endmost circumferential support element 22 to ends 54, 56 of rails 50.

As illustrated in FIG. 1, the stent portion 20 can include eight rails 50 that extend between the ends 54, 56. However, it is also contemplated that any number of rails 50 up to the number of peaks 12 along the circumference of the support element 22 could be used. For example, if the support elements 22 include three sets of peaks 12, then three rails 50 could be used. If the support elements included fourteen sets of peaks 12, then up to fourteen rails 50 could be used. In between the support elements 22 at the terminal ends 54, 56, the support elements 22 that are connected to each other by the bridge elements 24 are free to move along the rail(s) 50. These remaining support elements 22 slide along the rail(s) 50 so that the stent 50 can conform to the shape of the blood vessel. It is also contemplated that the terminal support elements 22 can move along the rails 50.

In the embodiment illustrated in FIG. 1, the circumferential support elements 22 include apertures 17 in the curved members 16 through which the rails 50 extend. Apertures 17 extend through the peaks 12 in a direction that is substantially parallel to the length of the stent portion 20. These apertures 17 retain and orient the supporting rail(s) 50 in a direction parallel to the length of the stent-graft 10. Also, in an embodiment, the rails 50 are completely contained within the walls (within the outer surface) of the stent-graft 10 so that they do not protrude beyond the outer surface of the stent-graft 10.

The struts 14 of the stent portion 20 can have substantially any radial thickness that provides them with the needed strength to support the graft portion 100 and a blood vessel when deployed and expanded within the vessel. Each strut 14 has a substantially low profile that will not damage the vessel as it is deployed. In one example, the struts 14 can have a radial thickness of between about 0.0001 inch and about 0.020 inch. In an embodiment, the radial thickness is about 0.002 inch to about 0.008 inch. In another embodiment, the struts 14 have a radial thickness of between about 0.004 inch and about 0.005 inch. These thicknesses provide the stent-graft 10 with the needed structural and expansion properties to support the graft 100, to support the vessel in which it is deployed and the longitudinal flexibility to conform to the natural elongated shape of the vessel.

In an embodiment, the areas of the curved members 16 are formed to have the same radial thickness as that of the struts 14 in order to accommodate the apparatus 17 and the received rail(s) 50. In another embodiment, the areas of the curved members 16 are formed with a greater radial thickness than the struts 14 in order to accommodate the apertures 17. For example, the radial thickness of the curved members 16 can be between about 0.001 inch and about 0.006 inch greater than that of the struts 14. The apertures 17 can have a diameter of about 0.005 inch for receiving the rails 50. Between the rails 50 where expansion occurs, the thickness could be about 0.004 inch. A stent portion 20 having 0.002 inch thick strut 14 walls could have a curved member 16 with a radial thickness of about 0.009 inch where the rails 50 are passed.

In the embodiments illustrated in FIGS. 9–15 and 17, the rails 50 extend through apertures 39 located at the first and second longitudinal peaks 34, 35 of the support elements 22. In a first embodiment, the areas of the support members 30 forming longitudinal peak 34 and longitudinal peak 35 and surrounding apertures 39 can have the same radial thickness as that of longitudinal struts 37 extending between the peaks 32–35. In an alternative embodiment, the areas surrounding apertures 39 can have a greater radial thickness than that of the longitudinal struts 37. As discussed above, the radial thickness of the areas surrounding apertures 39 can be between about 0.001 inch and about 0.006 inch greater than that of the struts 37. For example, a diamond shaped support member 30 having struts 37 with a radial thickness of about 0.002 inch could have a longitudinal peak 34, 35 with a radial thickness of between about 0.006 inch and about 0.009 inch.

Each aperture 39 can have a diameter that is large enough to slidably receive a rail 50. The diameter of each aperture 39 can be between about 0.0014 inch and about 0.012 inch. In an embodiment, the rail receiving area has an opening of between about 0.0014 inch and 0.006 inch. However, any diameter that slidably receives a rail 50 could also be used.

Figure 18:
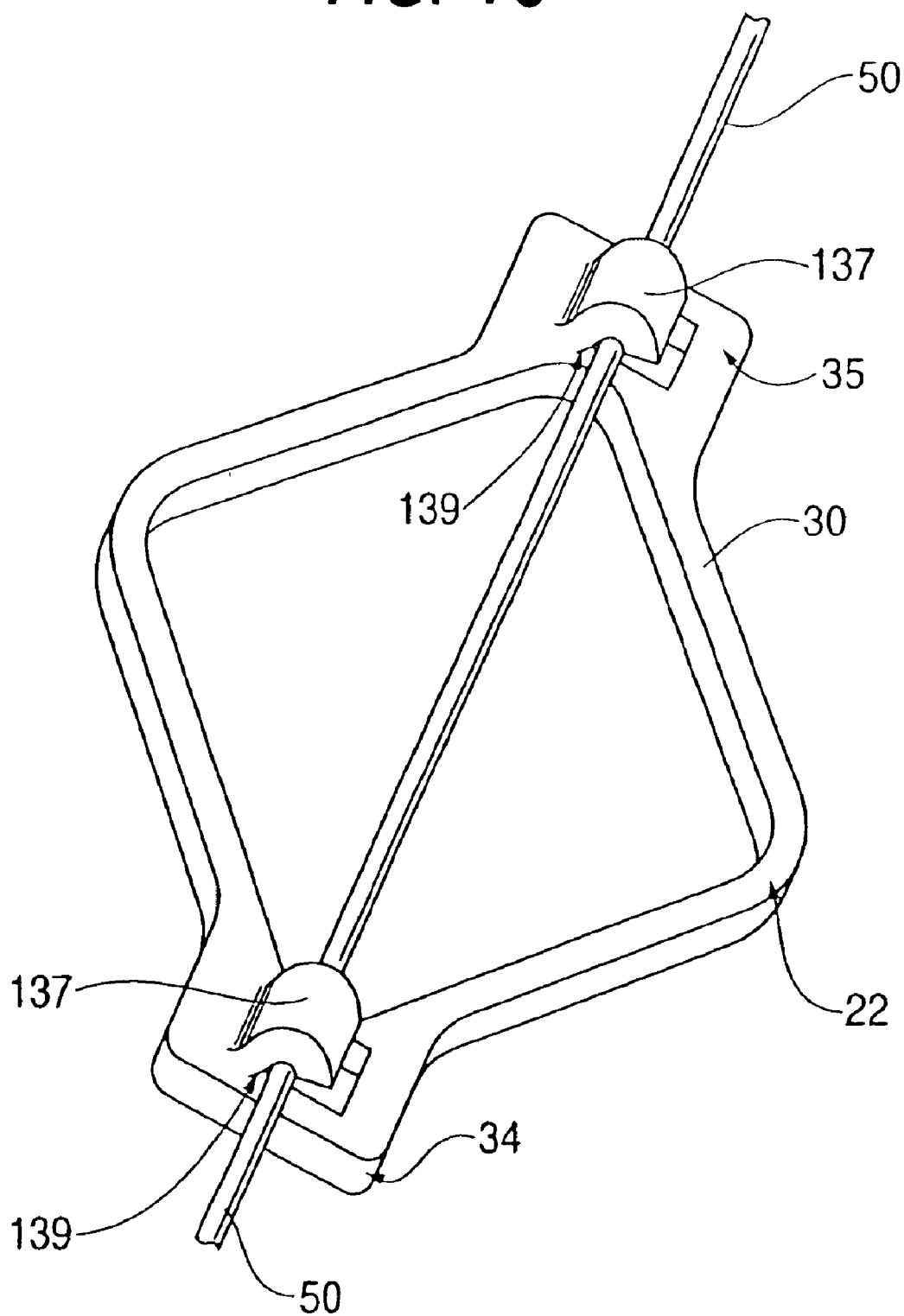
FIGS. 18–20 illustrate a vascular support member including rail receiving coupling members according to the present invention.
Figure 19:
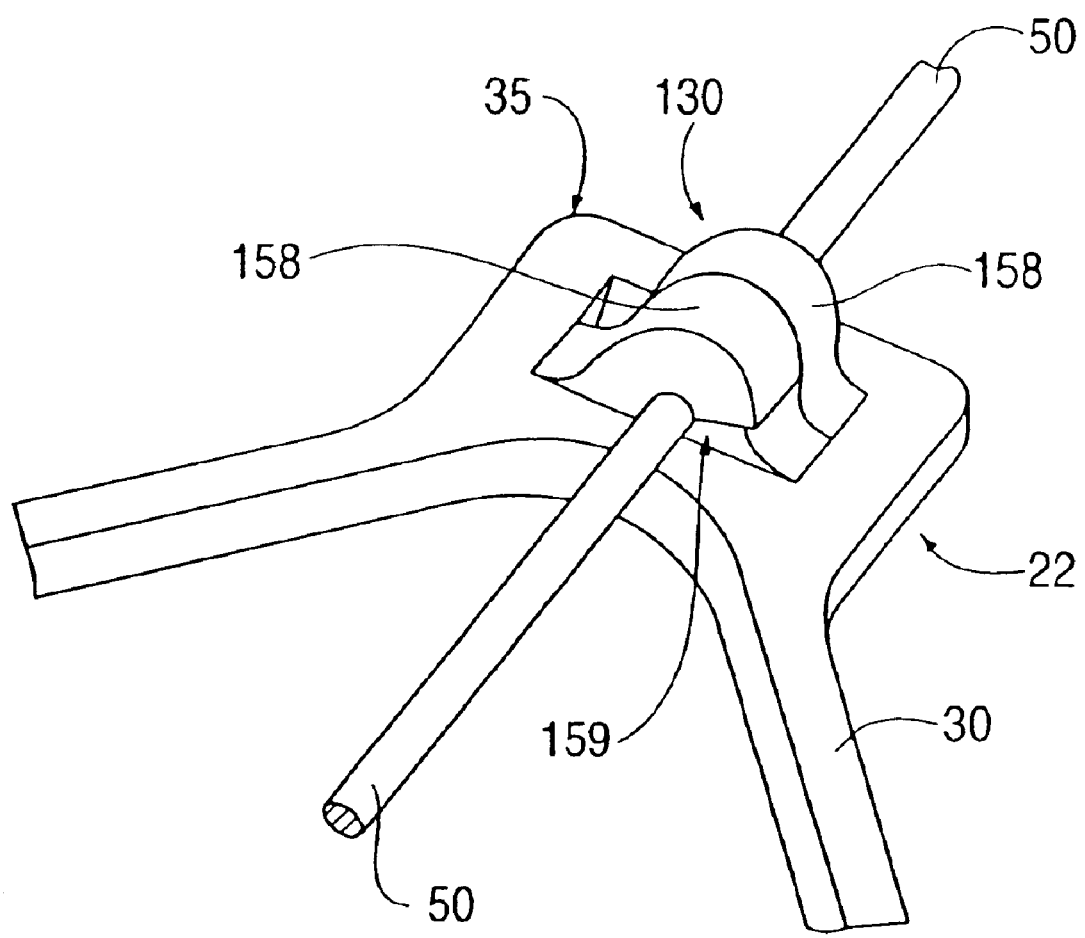
Figure 20:
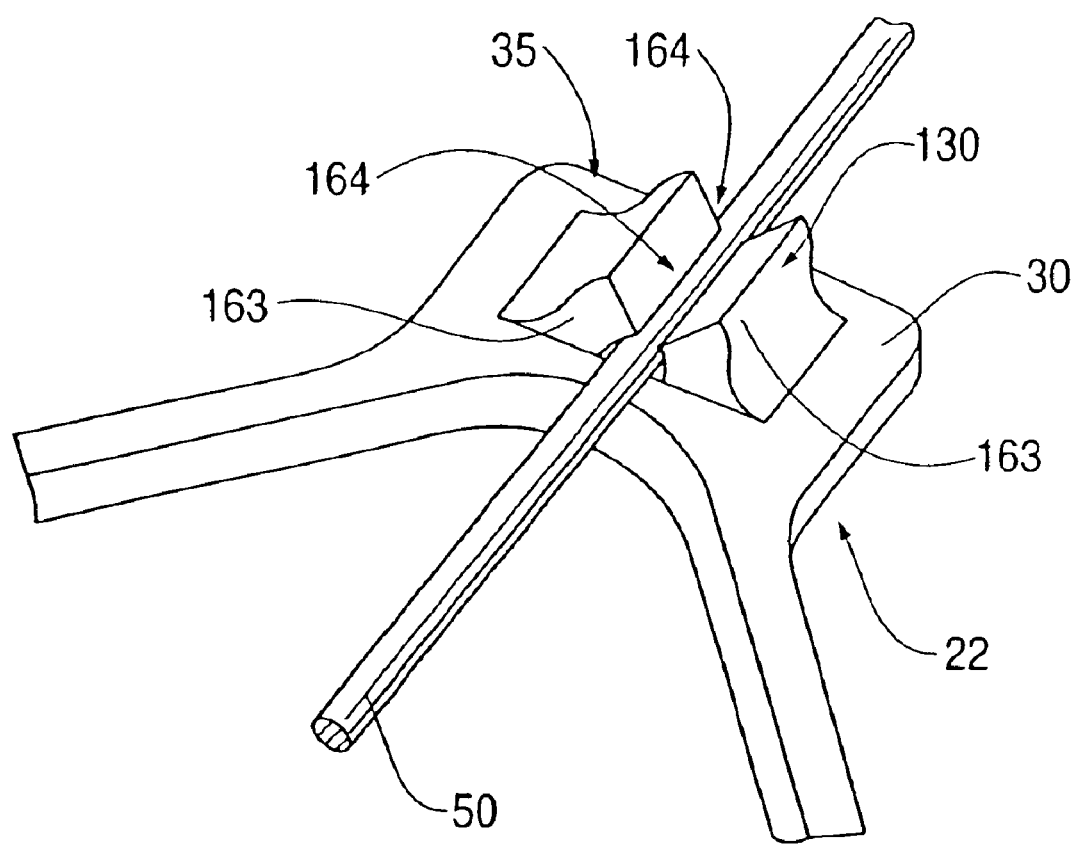

In alternative embodiments illustrated in FIGS. 18–20, the rails 50 are slidably received within rail receiving members 130 that extend from a surface of the support member 30 forming the support element 22. These rail receiving members 130 slidably couple a rail 50 to the support element 22. As illustrated, the rail receiving members 130 are located proximate the longitudinal peaks 34, 35 of their respective support member 30. However, the rail receiving members 130 could be located at other positions along the length of their respective support elements 22. Any of the above-discussed embodiments can include support elements 22 having the rail receiving members 130.

In a first embodiment illustrated in FIG. 18, the rail receiving members 130 are located proximate the longitudinal peaks 34, 35 of the support members 30. The receiving members 130 of this embodiment include an arm 137 with a groove 139 that receives the rail 50. The groove 139 has a bearing surface that is sized large enough to couple the support element 22 to the rail 50, while still permitting movement of the support element 22 along the rail 50 and relative to the graft portion 100.

In the embodiment illustrated in FIG. 19, each receiving member 130 can include two opposing arms 158 that are offset from each other along the length of the support member 30. Like arm 137, each arm 158 includes a groove 159 sized to couple the support member 30 to the rail 50 while permitting sliding movement of the support member and stent portion 20 relative to the rails 50.

In either embodiment illustrated in FIGS. 18 and 19, the arms 137, 158 can be formed by being punched, or otherwise mechanically formed, from a portion of its support member 30. Alternatively, the arms 137, 158 could be secured to their respective support members 30 by welding or other known connection techniques. Each arm 137, 158 can be formed to extend inwardly away from its support member 30 in the direction of the graft portion 100. In such an embodiment, the arms 137, 158 are not intended to contact the inner surface of the vessel into which the stent-graft 10 is deployed. Alternatively, the arms 137, 158 of the receiving members 130 can project outwardly away from the stent portion 100 and the outer surface of their support members 30 that are intended to contact the inner wall of the vessel in which the stent-graft 10 is deployed. As with the above-discussed embodiments, the grooves 139, 159 provide rail receiving areas having openings of between about 0.0014 inch and 0.012 inch. In an embodiment, the rail receiving areas of grooves 139, 159 has an opening of between about 0.0014 inch and 0.006 inch.

As illustrated in FIG. 20, the rail receiving members 130 can also include a pair of opposing, cooperating arms 163 that form a groove 164 into which the rail 50 can be snap fitted. The groove 164 is sized to receive the rail 50 such that the support member 30 is coupled to the rail 50 and free to move longitudinally along the rail 50 as discussed above with respect to the other embodiments. The arms 163 can be formed as discussed above with respect to the embodiments illustrated in FIGS. 18 and 19. Additionally, the arms 163 can extend from either the inner or outer surfaces of their respective support members 30 as discussed above with respect to the embodiments illustrated in FIGS. 18 and 19.

In any of the above-discussed embodiments, the illustrated graft portion 100 is formed of a well known biocompatible materials such as woven polyester including polyester terphthalate (PET, polyester, formerly available under the Dupont Trademark "Dacron"), polytetrafluroethylene (PTFE, Teflon) and fluorinated ethylene propylene (FEP, Teflon with additives for melt processing). Other polymer fabrics could be used including polypropylene, polyurethane, including porous polyurethane, and others. In an embodiment, the biocompatible material is expanded Polytetrafluroethylene (ePTFE). Methods for making ePTFE are well known in art, and are also described in U.S. Pat. No. 4,187,390 issued to Gore on Feb. 5, 1980, which is hereby incorporated herein by reference. The graft portion 100 can be formed of either woven or a non-woven material(s).

The porous structure of ePTFE consists of nodes interconnected by very small fibrils. The ePTFE material provides a number of advantages when used as a prosthetic vascular graft. The ePTFE is highly biocompatible, has excellent mechanical and handling characteristics, does not require preclotting with the patient's blood, heals relatively quickly following implantation, and is thromboresistant. Further, ePTFE has a microporous structure that allows natural tissue ingrowth and cell endothelialization once implanted into the vascular system. This contributes to long-term healing and graft patency.

The graft portion 100 can be surrounded by the rails 50 and the stent portion 20 as illustrated in FIGS. 1–17. In the first embodiment, illustrated in FIGS. 1–8, the stent-graft 10 includes a plurality of circumferentially extending, rail receiving coupling members 60 that are spaced from each other along the length of the graft portion 100. The rail receiving coupling members 60 eliminate the need to suture the stent portion 20 to the graft portion 100 at locations spaced from the ends of the graft portion 100.

Each coupling member 60 is sized to be circumferentially and longitudinally coextensive with a portion of the outer surface of the graft portion 100. The coupling members 60 can extend 360 degrees around the circumference of the graft portion 100 or only partially around the circumference of the graft portion 100. For example, each coupling member 60 may extend only about 270 or 180 degrees around the circumference of the graft portion 100. The coupling members 60 expand with the stent portion 20 and the graft portion 100 when the stent-graft 10 is expanded within a vessel using either self-expansion or a balloon.

Each coupling member 60 is formed of a known material such as those discussed above relating to the graft portion 100 including PTFE, ePTFE, FEP, woven PET (DACRON), PET film, or any polymer that can be bonded to the exterior of the graft portion 100 and permits the smooth and easy passage of the rails 50 through their associated passageways 62, hereinafter referred to as "openings 62". The material for each coupling member 60 can vary depending on the material used for the graft portion 100.

Figure 6:
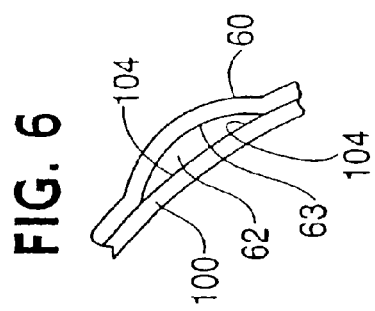
FIG. 6 illustrates an opening of a rail receiving coupling member along the circumference of the stent graft.
Figure 7:
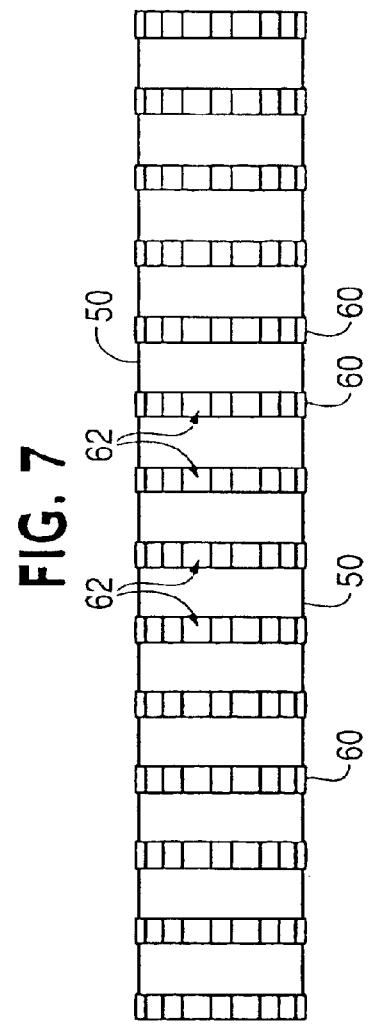
FIG. 7 is a side view of the rail receiving coupling members with at least two rails extending along the length of the stent-graft.

As shown in FIGS. 6 and 7, the openings 62 are formed between the inner surface of the coupling member 60 and the outer surface 104 of the graft portion 100 so that the openings 62 retain their open position before and after the rails 50 have been passed through. The openings 62 are equally or unequally spaced around the circumference of the coupling members 60. In an embodiment, the openings 62 are axially aligned along the length of the graft portion 100.

However, in an alternative embodiment, the openings 62 of adjacent coupling members 60 can be circumferentially offset relative to each other. The number of openings 62 circumferentially spaced about the coupling member 60 will equal the number of rails used for the stent-graft 10. For example, if the stent-graft 10 includes five rails 50, then each longitudinally spaced coupling member 60 could include at least five openings 62.

Figure 5:
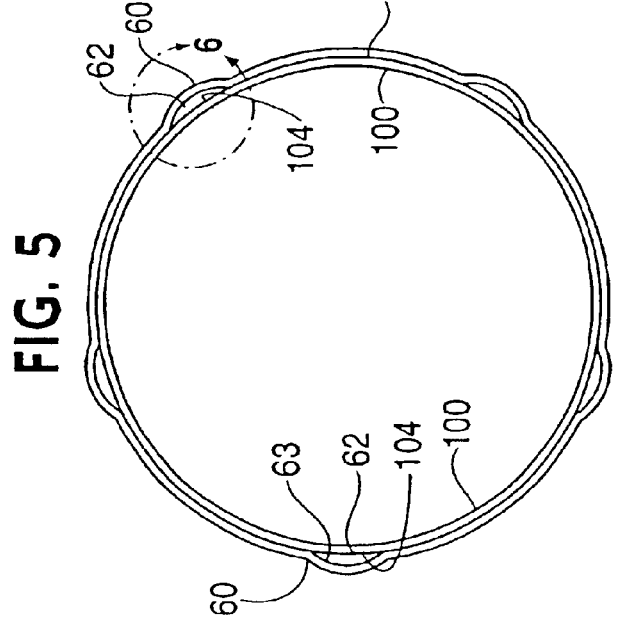
FIG. 5 is an end view of the graft portion and rail receiving coupling members shown in FIG. 3.

In an embodiment, the number of coupling members 60 will be equal to the number of support elements 22 that extend around the graft portion 100. As illustrated in FIG. 5, each coupling member 60 is formed of a single layer 64 of material secured to the outer surface of the graft portion 100 by ultrasonic welding, adhesive bonding, thermal fusing or other known manners. In this embodiment, the rails 50 extend between the inner surface 63 of each coupling member 60 at a respective opening 62 and the outer surface 104 of the graft portion 100.

In an alternative embodiment, the coupling member 60 includes a first circumferentially extending member secured to the outer surface 104 of the graft portion 100 and a second circumferentially extending member positioned over the first member. In this embodiment, the openings 62 are formed between the two circumferentially extending members.

In any of the above embodiments relating to FIGS. 1–8, the coupling members 60 are secured to the graft portion 100 and the stent portion 20 while receiving the rails 50 so that the coupling members 60 can move along and relative to the rails 50. The coupling members 60 can be secured to the support elements 22 by welding or other known conventional securing techniques. In an alternative embodiment, the coupling members 60 can extend through slots in the support elements 22 or they can be adhesively secured in recesses formed on the inner surfaces of the support elements 22.

Figure 9:
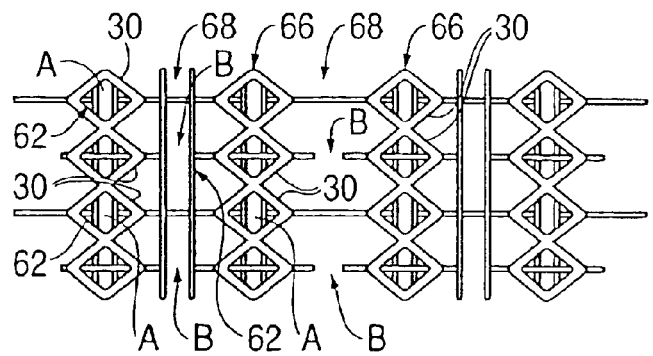
FIG. 9 illustrates a portion of an alternative stent-graft embodiment according to the present invention.
Figure 10:
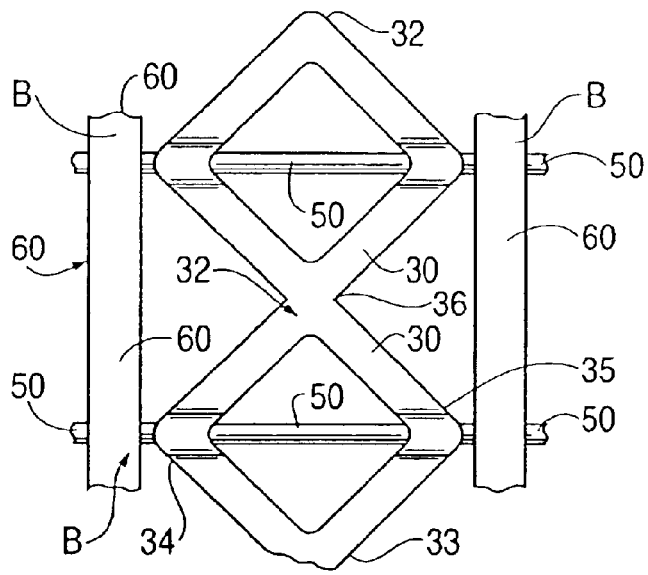
FIGS. 10 and 11 illustrate portions of an additional alternative stent-graft embodiment according to the present invention.
Figure 11:
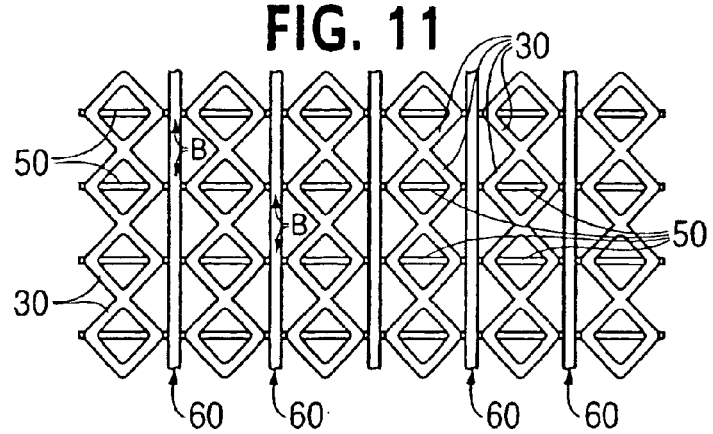

In the alternative embodiment illustrated in FIGS. 9–11, the coupling members 60 can be positioned along the length of the stent-graft 10 and oriented so that their openings 62 are circumferentially offset from the openings 62 of longitudinally adjacent coupling member(s) 66, 68. As shown in FIG. 9, coupling member 66 can have openings 62 that are positioned within the openings in circumferentially spaced support members 30 so that a respective rail 50 passes through the opening 62 in the coupling member 60 at point A that is between the longitudinal peaks 34, 35 of the support members 30. The coupling member 60 then passes under the circumferentially adjacent rail(s) 50 that extends through the immediately, circumferentially adjacent support member(s) 30 (See FIG. 9). The openings 62 of the immediately, longitudinally adjacent coupling member 68 are circumferentially offset from those of coupling member 66 so that the rail 50 passes through the openings 62 of the adjacent coupling member 68 at point B. As a result, immediately, longitudinally adjacent coupling members 60 (66, 68) slidably receive circumferentially spaced rails 50 at offset points. This can increase the stability of the stent-graft 10 without reducing its ability to conform to the shape of the vessel in which it is deployed.

In an alternative embodiment, shown in FIGS. 10 and 11, the longitudinally spaced coupling members 60 receive the rails 50 outside the support members 30 at point B. In this embodiment, the openings 62 of longitudinally adjacent coupling members 60 are circumferentially and longitudinally aligned.

Figure 12:
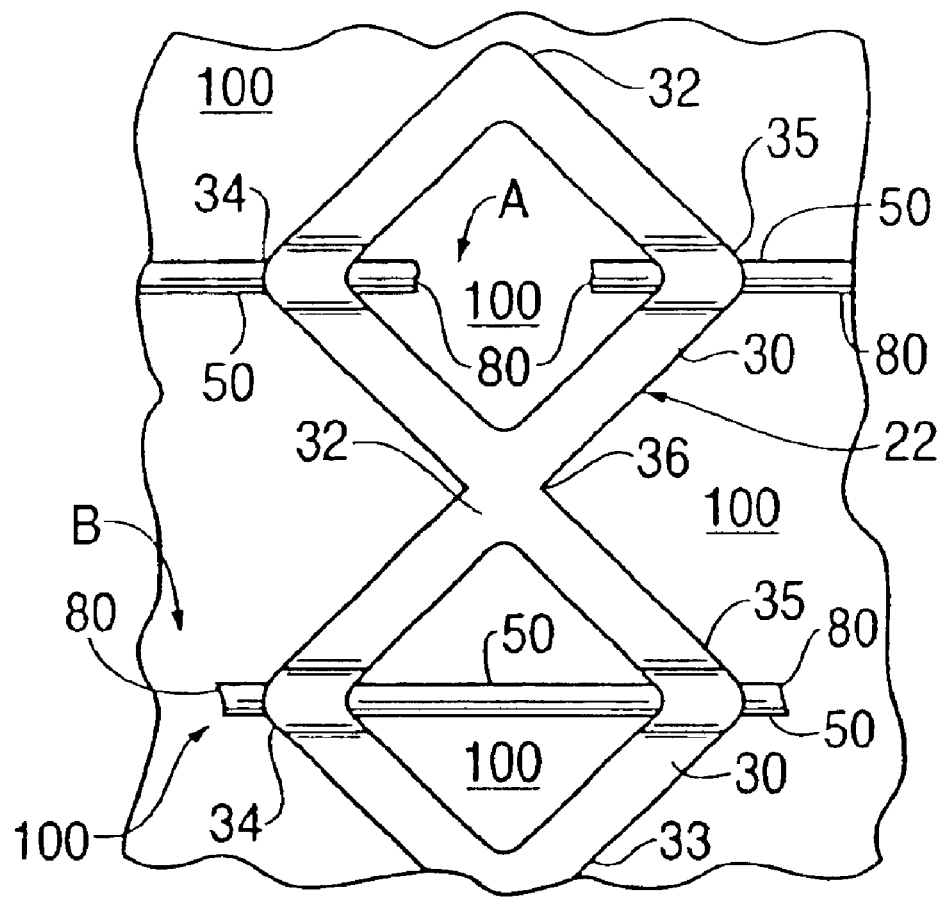
FIGS. 12–15 illustrate another alternative embodiment of the stent-graft according to the present invention in which the rails are extended through cauterized openings in the graft portion.
Figure 13:
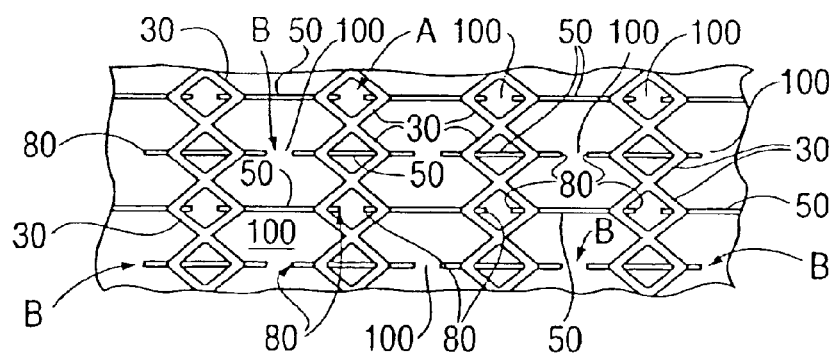
Figure 14:
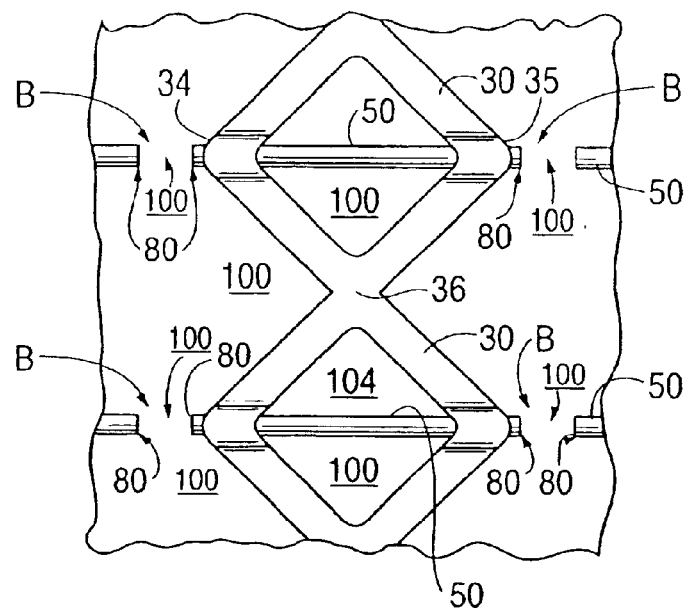
Figure 15:
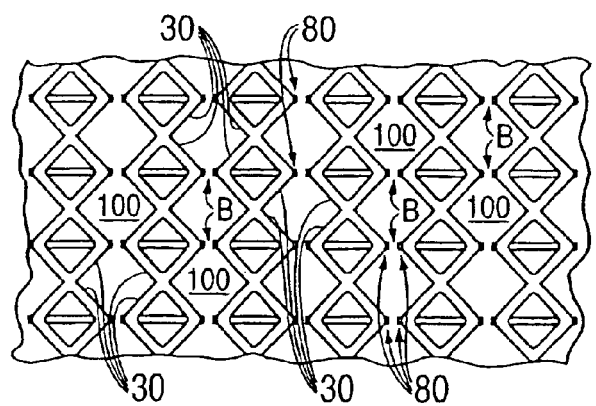

In the embodiments illustrated in FIGS. 12–15, the rails 50 could extend through cauterized openings in the graft portion 100 in place of using the coupling members 60. Hence, in these alternative embodiments, immediately, circumferentially adjacent rails 50 could be extended through cauterized openings 80 in the graft portion 100 at longitudinally and/or circumferentially offset points (A, B) as shown in FIGS. 9 and 12. Alternatively, the adjacent rails 50 could be extended through cauterized openings 80 the graft portion 100 at circumferentially and/or longitudinally aligned locations B, as shown in FIG. 14. In any of the above-discussed embodiments, the graft portion 100 will move with support elements 22 as the support elements 22 move along the rails 50.

Figure 16:
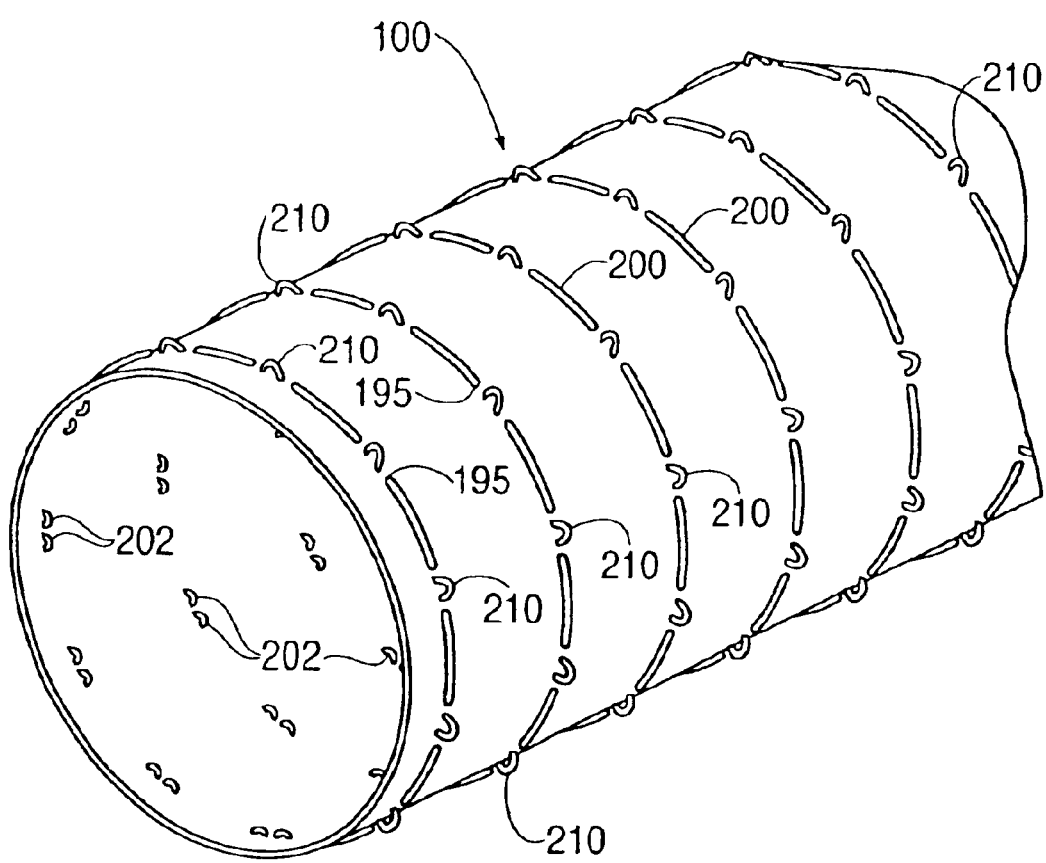
FIG. 16 illustrates a graft portion of a stent-graft according to another embodiment of the present invention.

In the embodiment illustrated in FIGS. 16 and 17, the rails 50 pass through circumferentially extending retainer coupling members 200, hereinafter referred to as "loops 200". Unlike coupling members 60 shown in FIG. 9, the loops 200 have interior regions 202 that pass through openings 195 in the graft portion 100 and extend along an inner surface of the graft portion 100. The openings 195 can be welded, cauterized or otherwise closed about the loops 200 using other known techniques. In an embodiment, the loops 200 can be formed of yarn that is stronger than the graft portion 100. In an embodiment, the loops 200 are formed of a PET, 80 denier loop yarn. The loops 200 can also be formed of any of the materials discussed above with respect to the graft portion 100. The loops 200 can also be formed of a solid polymer fiber, braid, film, or the like. It is also possible to bond or otherwise secure the loops 200 to the graft portion 100.

Portions of the loops 200 on the exterior of the graft portion 100 and in-between the interior regions 202 form arches 210 along the outer surface of the graft portion 100. The arches 210 slidably receive the rails 50 so that the graft portion 100 can move along the rails 50 and relative to the support elements 22. While rounded arches 210 are illustrated, any shaped opening that slidably receives the rails 50 can be used. For example, the opening of the arches 210 can include a rectangular, elliptical or triangular shape. The arches 210 each include an opening sized to receive the rails 50. These opening can be between about 0.0014 inch and about 0.012 inch. In an embodiment, the arch openings can be between about 0.0014 inch and about 0.006 inch. In an embodiment, the arch openings can be about 0.005 inch.

Each arch 210 is spaced from circumferentially spaced arches 210 by a distance that is substantially equal to the circumferential spacing of the adjacent rails 50. The adjacent arches 210 can be equally spaced from each other around the circumference of the graft portion 100. Alternatively, adjacent arches 210 can be circumferentially spaced at different intervals around the circumference of the graft portion 100 to provide different flexion capabilities to the stent graft 10. Each arch 210 can be spaced from an adjacent arch 210 by a distance of about 0.10 inch to about 0.30 inch. In one embodiment, adjacent arches 210 are spaced from each other by a distance of about 0.155 inch.

Figure 17:
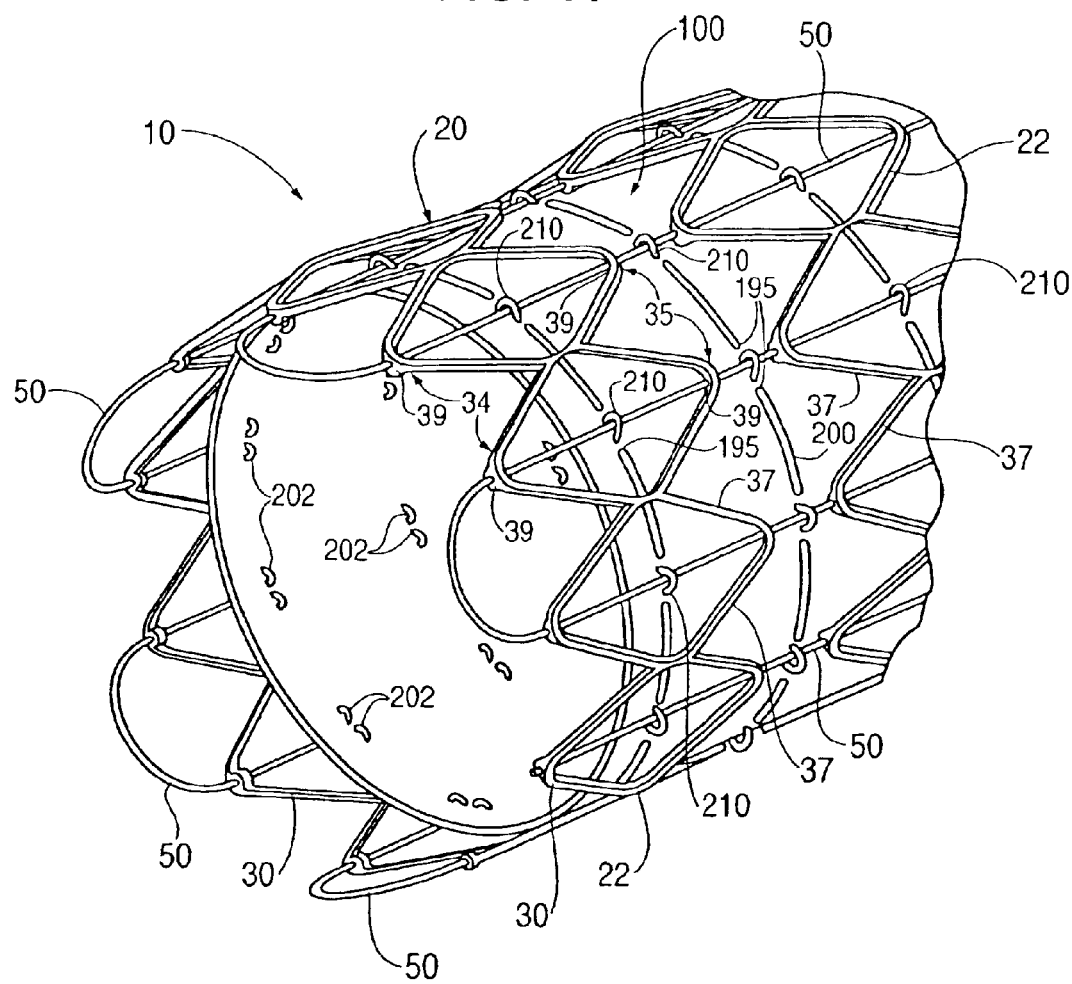
FIG. 17 illustrates a stent-graft according to the present invention including the graft portion illustrated in FIG. 16.

The support elements 22 comprise the diamond shaped support members 30 shown in FIGS. 9 and 17. However, as with the above-discussed embodiments, other known shapes may also be used. Similar to the embodiments illustrated in FIGS. 9–15, the support elements 22 shown in FIG. 17 include apertures 39 and are free of a connection to the loops 200. The support elements 22 (FIG. 17) are moveable along the rails 50 in a direction that is substantially parallel to the length of the graft portion 100 as discussed above.

The movement of the support elements 22 along the length of the stent-graft 10 and relative to the rails 50 and graft portion 100 can be limited by one or both of the longitudinal peaks 34, 35 abutting against a support element 200. As shown in FIG. 17, the arches 210 of the loops 200 can act as a stop for the longitudinal movement of the support element 22. Therefore, the total distance that the support elements 22 move along the rails 50 can be controlled and limited by the spacing between the loops 200 along the length of the graft portion 100. In one embodiment, each loop 200 can be spaced from adjacent loops 200 along the length of the graft portion 100 by the same distance as the coupling members 60 so that the support elements 22 can move a distance that permits the stent-graft 10 to conform to the shape of the vessel in which the stent-graft 10 is deployed. The spacing between adjacent loops 200 (and 60) can be less than the distance that each support element 22 extends in a direction parallel to the length of the stent-graft 10.

Unlike the other embodiments (for example the embodiment illustrated in FIG. 1), each support elements 22 illustrated in FIG. 17 is free of a connection to a longitudinally adjacent support element 22 by a bridging element. As a result, the support elements 22, illustrated in FIG. 17, can move independently relative to each other along the length of the graft portion 100. Also, like the embodiments discussed above, the rails 50 can include a single, continuous member with multiple turns (FIG. 17), a plurality of separate members with at least one turn that are circumferentially spaced from adjacent members around the graft portion 100, or separate, individual members that are free of turns and that are free of a direct, secured attachment to an adjacent rail 50. As used herein, the term "rail" includes each of these arrangements.

In another alternative embodiment, the graft portion 100 can include integral, spaced areas that receive the rails 50 formed of the material used to form the graft portion 100. These spaced areas have an increased thickness with respect to the remainder of the graft portion 100.

The present invention also includes introducing an agent, including those set forth in U.S. patent application Ser. No. 60/426,366, which is hereby incorporated by reference, into a body using the above-discussed stent-graft 10. In a preferred embodiment, the agent(s) is carried by one or more of the rails 50 or the graft portion 100 and released within the body over a predetermined period of time. For example, these stents can deliver one or more known agents, including therapeutic and pharmaceutical drugs, at a site of contact with a portion of the vasculature system or when released from a carrier as is known. These agents can include any known therapeutic drugs, antiplatelet agents, anticoagulant agents, antimicrobial agents, antimetabolic agents and proteins. These agents can also include any of those disclosed in U.S. Pat. No. 6,153,252 to Hossainy et al. and U.S. Pat. No. 5,833,651 to Donovan et al., both of which are hereby incorporated by reference in their entirety. Local delivery of these agents is advantageous in that their effective local concentration is much higher when delivered by the stent than that normally achieved by systemic administration.

The rails 50, which have a relatively low elastic modulus (i.e. low force to elastic deformation) in their transverse direction, may carry one or more of the above-referenced agents for applying to a vessel as the vessel moves into contact with the agent carrying rail(s) 50 after deployment of the stent-graft 10 within the vessel. These agents can be applied using a known method such as dipping, spraying, impregnation or any other technique described in the above-mentioned patents and patent applications that have been incorporated by reference. Applying the agents to the rails 50 avoids the stresses at focal areas as seen in the struts of traditional stents. In this manner drug coatings applied to the stent rails 50 may be used with support elements formed of materials that are otherwise unsuitable for coating.

It is contemplated that the various elements of the present invention can be combined with each other to provide the desired flexibility. For example, the rails 50 can be formed of one or more radiopaque materials. Additionally, the support element designs can be altered and various support element designs that permit the passage of the rails could be used. Similarly, the number, shape, composition and spacing of the rail elements can be altered to provide the stent with different properties. Additionally, the device can have varying numbers and placement of the bridge elements. The properties of any individual stent would be a function of the design, composition and spacing of the support elements, rails and bridge elements.

Thus, while there have been shown and described and pointed out fundamental novel features of the present invention as applied to preferred embodiments thereof, it will be understood that various omissions and substitutions and changes in the form and details of the devices illustrated, and in their operation, and in the method illustrated and described, may be made by those skilled in the art without departing from the spirit of the invention as broadly disclosed herein.

What is claimed is:

1. A stent-graft comprising:
   an elongated stent portion extending about an axis;
   a graft portion being at least partially coextensive with said stent portion; and
   at least one rail element extending along a length of said stent-graft, each rail element being movably coupled to said stent portion and/or said graft portion such that at least a portion of said stent portion and said graft portion are freely movable along a portion and relative to each rail element.

2. The stent-graft according to claim 1, wherein said graft portion includes circumferentially extending coupling members spaced along said axis, and wherein said at least one rail element is slidably connected to said graft portion by a plurality of said longitudinally spaced circumferentially extending coupling members.

3. The stent-graft according to claim 2, wherein said stent portion includes a plurality of circumferential support elements.

4. The stent-graft according to claim 3, wherein said circumferential support elements comprise apertures for receiving said at least one rail element.

5. The stent-graft according to claim 3, wherein adjacent support elements are connected together by a bridge member.

6. The stent-graft according to claim 3, wherein each support element is free of a direct connection to an adjacent support element.

7. The stent-graft according to claim 3, wherein each support element is free of a direct connection to said circumferentially extending coupling members and said graft portion.

8. The stent-graft according to claim 3, wherein said support elements each include peaks and troughs, and wherein a plurality of axially spaced peaks include openings for receiving said at least one rail element.

9. The stent-graft according to claim 3, wherein each said support element includes diamond shaped support members distributed along its circumferential length.

10. The stent-graft according to claim 3, wherein said circumferentially extending coupling members limit the longitudinal movement of said support elements along the length of said at least one rail element.

11. The stent-graft according to claim 3, wherein the distance between spaced adjacent circumferentially extending coupling members is less than the distance each said support element extends in a direction parallel to said axis.

12. The stent-graft according to claim 2, wherein said at least one rail element extends through a sealed opening in said graft portion.

13. The stent-graft according to claim 12, wherein said opening is cauterized.

14. The stent-graft according to claim 2 wherein said coupling members are secured to said graft portion.

15. The stent-graft according to claim 2, wherein said circumferentially extending coupling members comprise a first portion that extends within said graft portion and a second portion that forms an arch along an outer surface of said graft portion for receiving said at least one rail element.

16. The stent-graft according to claim 15 wherein each said circumferentially extending coupling member includes a yarn extending through sealed openings within said graft portion.

17. The stent-graft according to claim 2 wherein said at least one rail element extends through openings in said graft portion and said circumferentially extending coupling members.

18. The stent-graft according to claim 1, wherein said graft portion extends between terminal ends of said stent portion.

19. The stent-graft according to claim 1, wherein said graft portion is formed of ePTFE.

20. The stent-graft according to claim 1, wherein said stent portion comprises a plurality of support elements spaced along the length of said axis, each support element comprising a plurality of circumferentially connected support members having a plurality of elongated struts and curved sections that connect longitudinally adjacent struts.

21. The stent-graft according to claim 20, wherein each said support member includes at least one rail receiving member for slidably coupling each said support member to said at least one rail element.

22. The stent-graft according to claim 21, wherein said at least one rail receiving member includes an arm having a groove for slidably receiving said at least one rail element.

23. The stent-graft according to claim 21, wherein said at least one rail receiving member includes a pair of opposing arms, each said arm having a groove for slidably receiving said at least one rail element.

24. The stent-graft according to claim 21, wherein said at least one rail receiving member includes a rail receiving groove formed by a pair of opposing arms.

25. The stent-graft according to claim 1 wherein at least a portion of said at least one rail element extends substantially parallel to said axis.

26. A stent-graft for positioning within a portion of a mammalian body, said stent-graft comprising:
   a graft portion extending about an elongated axis;
   an elongated stent portion being at least partially coextensive with and surrounding at least a portion of said graft portion, said stent portion including a plurality of support elements spaced from each other along the length of said stent graft; and
   at least one rail element extending along a length of said stent-graft, said at least one rail element slidably coupled to said stent portion such that said stent portion and graft portion are movable along said at least one rail element and said stent portion is moveable relative to said graft portion.

27. The stent-graft according to claim 26, wherein said at least one rail element is slidably coupled to said graft portion.

28. The stent-graft according to claim 26, wherein said stent portion is free of a direct connection to said graft portion.

29. The stent-graft according to claim 26, wherein said graft portion includes circumferentially extending coupling members spaced along said axis, and wherein said at least one rail element is slidably connected to said graft portion by said longitudinally spaced circumferentially extending coupling members.

30. The stent-graft according to claim 29, wherein said support elements include a plurality of circumferentially extending support members.

31. The stent-graft according to claim 30, wherein said circumferential support elements comprise apertures for receiving said at least one rail element.

32. The stent-graft according to claim 30, wherein each said support element includes diamond shaped support members distributed along its circumferential length.

33. The stent-graft according to claim 30, wherein the distance between spaced adjacent circumferentially extending coupling members is less than the distance each said support element extends in a direction parallel to said axis.

34. The stent-graft according to claim 30 wherein said coupling members are secured to said graft portion.

35. The stent-graft according to claim 29, wherein said circumferentially extending coupling members comprise a first portion that extends within said graft portion and a second portion that forms an arch along an outer surface of said graft portion for receiving said at least one rail element.

36. The stent-graft according to claim 29, wherein said at least one rail element extends through openings in said graft portion and said circumferentially extending coupling members.

37. The stent-graft according to claim 29, wherein said circumferentially extending coupling members limit the longitudinal movement of said support elements along the length of said at least one rail element.

38. The stent-graft according to claim 29 wherein each said circumferentially extending coupling member includes a yarn extending through sealed openings within said graft portion.

39. The stent-graft according to claim 26, wherein adjacent circumferential support elements are connected together by a bridge member.

40. The stent-graft according to claim 26, wherein each support element is free of a direct connection to an adjacent support element.

41. The stent-graft according to claim 26, wherein each support element is free of a direct connection to said circumferentially extending coupling members and said graft portion.

42. The stent-graft according to claim 26, wherein said graft portion extends between terminal ends of said stent portion.

43. The stent-graft according to claim 26, wherein said graft portion is formed of ePTFE.

44. The stent-graft according to claim 26, wherein said at least one rail element extends through a sealed opening in said graft portion.

45. The stent-graft according to claim 44, wherein said opening is cauterized.

46. The stent-graft according to claim 26, wherein said support elements each include peaks and troughs, and wherein a plurality of axially spaced peaks include openings for receiving said at least one rail element.

47. The stent-graft according to claim 26, wherein said support elements each comprise a plurality of circumferentially connected support members having a plurality of elongated struts and curved sections that connect longitudinally adjacent struts.

48. The stent-graft according to claim 43, wherein each said support member includes at least one rail receiving member for slidably coupling each said support member to said at least one rail element.

49. The stent-graft according to claim 48, wherein said at least one rail receiving member includes an arm having a groove for slidably receiving said at least one rail element.

50. The stent-graft according to claim 48, wherein said at least one rail receiving member includes a pair of opposing arms, each said arm having a groove for slidably receiving said at least one rail element.

51. The stent-graft according to claim 48, wherein said at least one rail receiving member includes a rail receiving groove formed by a pair of opposing arms.

52. The stent-graft according to claim 26 wherein at least a portion of said at least one rail element extends substantially parallel to said axis.

* * * * *